US011602595B2

(12) United States Patent
Lee

(10) Patent No.: US 11,602,595 B2
(45) Date of Patent: Mar. 14, 2023

(54) MEDICAL FLUID INJECTOR INCLUDING BOLUS COUNTER

(71) Applicant: Woo Suk Lee, Seoul (KR)

(72) Inventor: Woo Suk Lee, Seoul (KR)

(*) Notice: Subject to any disclaimer, the term of this patent is extended or adjusted under 35 U.S.C. 154(b) by 243 days.

(21) Appl. No.: 16/856,250

(22) Filed: Apr. 23, 2020

(65) Prior Publication Data

US 2020/0246542 A1 Aug. 6, 2020

Related U.S. Application Data

(63) Continuation of application No. PCT/KR2019/014098, filed on Oct. 24, 2019.

(30) Foreign Application Priority Data

Dec. 5, 2018 (KR) .................. 10-2018-0154925

(51) Int. Cl.
*A61M 5/14* (2006.01)
*A61M 5/168* (2006.01)
*A61M 39/24* (2006.01)
*A61M 5/142* (2006.01)

(52) U.S. Cl.
CPC .... *A61M 5/16886* (2013.01); *A61M 5/16818* (2013.01); *A61M 39/24* (2013.01); *A61M 5/1424* (2013.01); *A61M 5/168* (2013.01); *A61M 2005/1405* (2013.01); *A61M 2205/583* (2013.01)

(58) Field of Classification Search
CPC ........ A61M 2005/0405; A61M 5/1424; A61M 5/168
See application file for complete search history.

(56) References Cited

U.S. PATENT DOCUMENTS

| 4,528,933 A * | 7/1985 | Allen ................. A61J 7/04 215/230 |
| 2012/0053556 A1 | 3/2012 | Lee |
| 2013/0116630 A1 | 5/2013 | Valle et al. |

FOREIGN PATENT DOCUMENTS

| JP | 2002-058739 A | 2/2002 |
| JP | 2002058739 A * | 2/2002 |
| JP | 4699588 B2 | 6/2011 |
| JP | 2011-224182 A | 11/2011 |
| KR | 10-1126213 B1 | 3/2012 |
| KR | 10-2013-0056898 A | 5/2013 |
| KR | 10-2014-0005182 A | 1/2014 |

(Continued)

OTHER PUBLICATIONS

International Search Report (PCT/KR2019/014098), WIPO, dated Feb. 4, 2020.

(Continued)

*Primary Examiner* — Nathan R Price
*Assistant Examiner* — Tania Ismail
(74) *Attorney, Agent, or Firm* — Park & Associates IP Law Office

(57) ABSTRACT

The present invention relates to a medical fluid injector. In particular, by including a bolus counter that provides the correct number of bolus injections, it is possible to prevent the problem of excessive administration of a medical fluid due to frequent bolus injections through the management of the number of bolus injections, and increase effectiveness of treatment through the establishment of a treatment strategy based on the number of bolus injections provided.

5 Claims, 10 Drawing Sheets

(56) References Cited

FOREIGN PATENT DOCUMENTS

| KR | 10-2015-0039350 A | 4/2015 |
|---|---|---|
| KR | 10-1638969 B1 | 7/2016 |

OTHER PUBLICATIONS

Korean Office Action (KR 10-2018-0154925), KIPO, dated Mar. 30, 2020.

* cited by examiner

MEDICAL FLUID INJECTOR INCLUDING BOLUS COUNTER

REFERENCE TO RELATED APPLICATIONS

This is a continuation of International Patent Application PCT/KR2019/014098 filed on Oct. 24, 2019, which designates the United States and claims priority of Korean Patent Application No. 10-2018-0154925 filed on Dec. 5, 2018, the entire contents of which are incorporated herein by reference.

FIELD OF THE INVENTION

The present invention relates to a medical fluid injector used for administering a liquid analgesic to a patient.

BACKGROUND OF THE INVENTION

In general, opioid analgesics are administered to a patient in need of pain management for the purpose of pain relief. While excessive administration of opioid analgesics may cause cardiopulmonary arrest in patients due to difficulty in breathing due to muscle stiffness or the like, insufficient administration may lead to a reduced efficacy. Due thereto, it is very important to administer a constant amount within a predetermined range. Therefore, in this field, a medical fluid injector that provides a constant amount of an analgesic and other medical fluids to a patient has been used, and examples of such a medical fluid injector have been disclosed in Korean Patent No. 10-1126213, and Korean Patent No. 10-1638969. Referring to these patent documents, a medical fluid injector according to the related art is as follows.

The medical fluid injector according to the related art is configured to continuously inject a patient with a medical fluid through a first transfer line, and additionally inject the patient with the medical fluid when necessary through a second transfer line and a bolus device to temporarily increase the amount of the medical fluid administered to the patient.

The medical fluid injector according to the related art is configured to continuously inject a medical fluid to a patient through a first transfer line, and additionally inject the medical fluid when necessary through a second transfer line and a bolus device to temporarily increase the amount of the medical fluid administered to the patient. The bolus device includes a bolus bag provided on the second transfer line, and is configured such that when a bolus button is operated, the bolus bag is pressurized to cause a medical fluid stored in the bolus bag to be discharged.

According to the bolus device, the medical fluid injector according to the related art allows the patient to operate the bolus button by himself/herself to additionally administer the medical fluid depending on patient's own conditions. However, in order for the patient to manage the number of bolus injections according to the operation of the bolus button to prevent excessive administration of the medical fluid, the patient himself/herself has to count and recognize the number of bolus injections, and therefore this inevitably results in the problem of inconvenience in use. Furthermore, because a manager (doctor or the like) cannot accurately ascertain the number of bolus injections made by the patient, there is a problem that it is difficult to maximize effectiveness of treatment by controlling of the administration amount of the medical fluid.

SUMMARY OF THE INVENTION

An embodiment of the present invention is to provide a medical fluid injector that enables a user (patient, manager, or the like) to more accurately recognize the number of bolus injections.

According to one aspect of the present invention, there is provided a medical fluid injector, including: a housing having an upper end (ceiling) provided with a button opening; a bolus bag connected to a medical fluid transfer line to store a medical fluid from an upstream side and discharge the stored medical fluid to a downstream side, and disposed inside the housing; a bolus button including a button movably inserted into the button opening so at to be movable upwardly and downwardly, and a push rod extending downwardly from the button and configured to push the bolus bag to cause the medical liquid in the bolus bag to be discharged when the button is moved downwardly; and a bolus counter configured to operate with a force that the button is moved downwardly and count the number of bolus injections according to operation of the bolus button.

A stop flange configured to be in contact with the upper end of the housing to restrict upward movement of the button may be provided between the button and the push rod.

The bolus counter may include: a count disc rotatably fitted over an outer circumference of the push rod; first teeth arranged on an upper surface of the count disc at an interval of a predetermined angle in a circumferential direction, and each of which includes a first inclined surface inclined in the circumferential direction; at least one second tooth provided on a lower surface of the stop flange to have a second inclined surface corresponding to the first inclined surface, and configured such that when the second tooth is moved downwardly, the second inclined surface is brought into contact with the first inclined surface to cause the count disc to be rotated; an elastic member imparting elastic force to the count disc to allow the count disc to be moved upwardly; a spacer protruding to above a height of the first teeth from a peripheral portion of the count disc and configured such that when the count disc is moved upwardly by the elastic member, the spacer is brought into contact with a lower surface of the upper end of the housing to cause the first inclined surface and the second inclined surface corresponding to each other to be spaced apart from each other; guide teeth arranged on an outer surface of the count disc in a circumferential direction at the interval of the predetermined angle, and each of which has a first guide surface formed at an upper portion thereof to be inclined in the same circumferential direction as the first inclined surface; and a guide configured such that a guide groove into which at least one of the guide teeth is fitted when the count disc is moved upwardly by the elastic member is provided on an inner circumference of the housing, and a second guide surface corresponding to the first guide surface is formed at a lower portion thereof, wherein when the count disc is moved downwardly by the bolus button, the count disc may be rotated by a partial angle of the predetermined angle by the first inclined surface and the second inclined surface corresponding to each other, and when the count disc is moved upwardly by the elastic member, the count disc may be rotated by a remaining angle of the predetermined angle by the first guide surface and the second guide surface to a position where the second inclined surface corresponds to the other first inclined surface neighboring thereto.

The spacer may be formed in a ring shape, with an upper surface provided with an indicator indicating the number of bolus injections, and a number indicating opening exposing the indicator may be provided at the upper end of the housing.

The bolus bag may include: a container having a medical fluid inlet and a medical fluid outlet, with an open upper portion; an expansion sheet shielding the open upper portion of the container; and a check valve opening and closing the medical fluid outlet, wherein the expansion sheet may be expanded by the medical fluid introduced into the container through the medical fluid inlet, and the check valve may be configured to be opened when the expansion sheet is pressurized by the push rod and a pressure in the container is increased thereby.

The check valve may include: a movable member passing through the medical fluid outlet so as to be movable along the medical fluid outlet; an opening/closing member coupled to the movable member to open and close an outlet end of the medical fluid outlet according to a moving direction of the movable member; and an elastic member imparting elastic force to the movable member in a direction in which the opening/closing member is closed, wherein when the expansion sheet is pressurized by the push rod and the pressure in the container is increased thereby (i.e., when the pressure in the container is greater than the elastic force of the elastic member of the check valve), the movable member may be moved while overcoming the elastic force of the elastic member of the check valve in a direction in which the opening/closing member is opened, thereby causing the medical fluid outlet to be opened.

A button cover protecting the button protruding through the button opening may be formed at the upper end of the housing so as to entirely surround remaining regions except for any one of peripheral regions around the button.

The button cover may be provided with a clip for carrying purposes, or a string connection hole for connection of a portable string.

The medical fluid injector may further include: a button holder maintaining a pressurized state of the bolus bag pressurized by the button moved downwardly, wherein the button holder may include: a body pressing the button; and legs arranged at a lower portion of the body in the circumferential direction, and each of which has a lower end bent in a circumferential direction, slots into which the respective legs are inserted may be provided at the upper end of the housing in a circumferential direction, and the legs may be configured to be prevented from separation when inserted into the slots and rotated, and have a length that allows the button to be pressed by the body when the respective lower ends of the legs are caught in the slots.

According to an embodiment of the present invention, it is possible to accurately count the number of bolus injections by a bolus counter and provide the count to a user such as a patient, a manager, or the like. Furthermore, due thereto, it is possible to prevent the problem that excessive administration of medical fluid may occur.

Furthermore, it is possible to achieve an increased effectiveness of treatment through the establishment of a treatment (pain management) strategy based on the number of bolus injections provided.

DETAILED DESCRIPTION OF THE INVENTION

Hereinafter, exemplary embodiments of the present invention will be described with reference to the accompanying drawings.

Embodiments of the present invention can be used to administer a medical fluid such as an analgesic or an antibiotic to a subject, such as a patient or the like.

The configuration and the like of the medical fluid injector according to the first embodiment of the present invention are illustrated in FIGS. 1 to 9.

Figure 1:
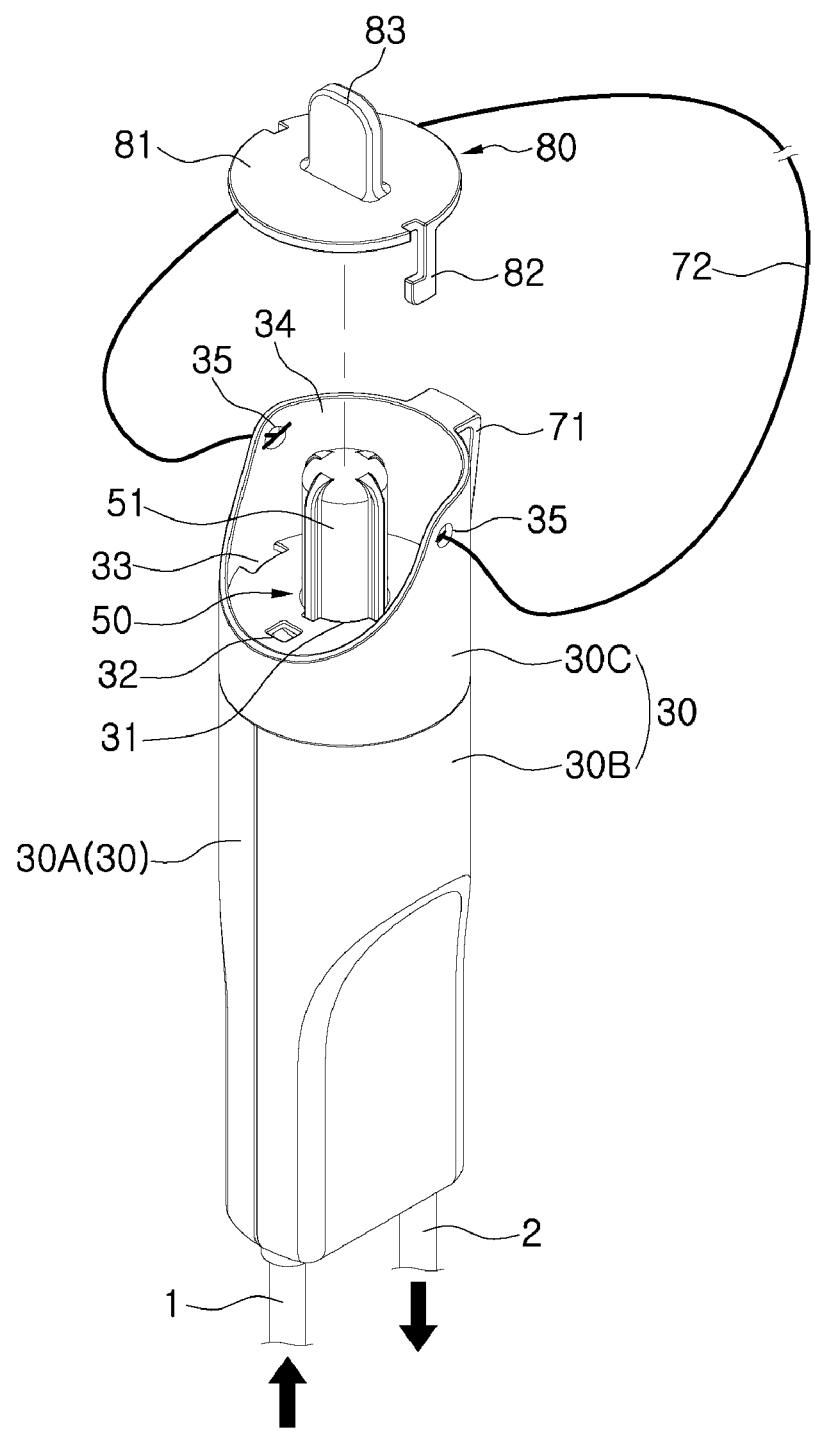
FIGS. 1 and 2 are perspective views illustrating a state in which a medical fluid injector according to a first embodiment of the present invention is viewed from different directions.
Figure 2:
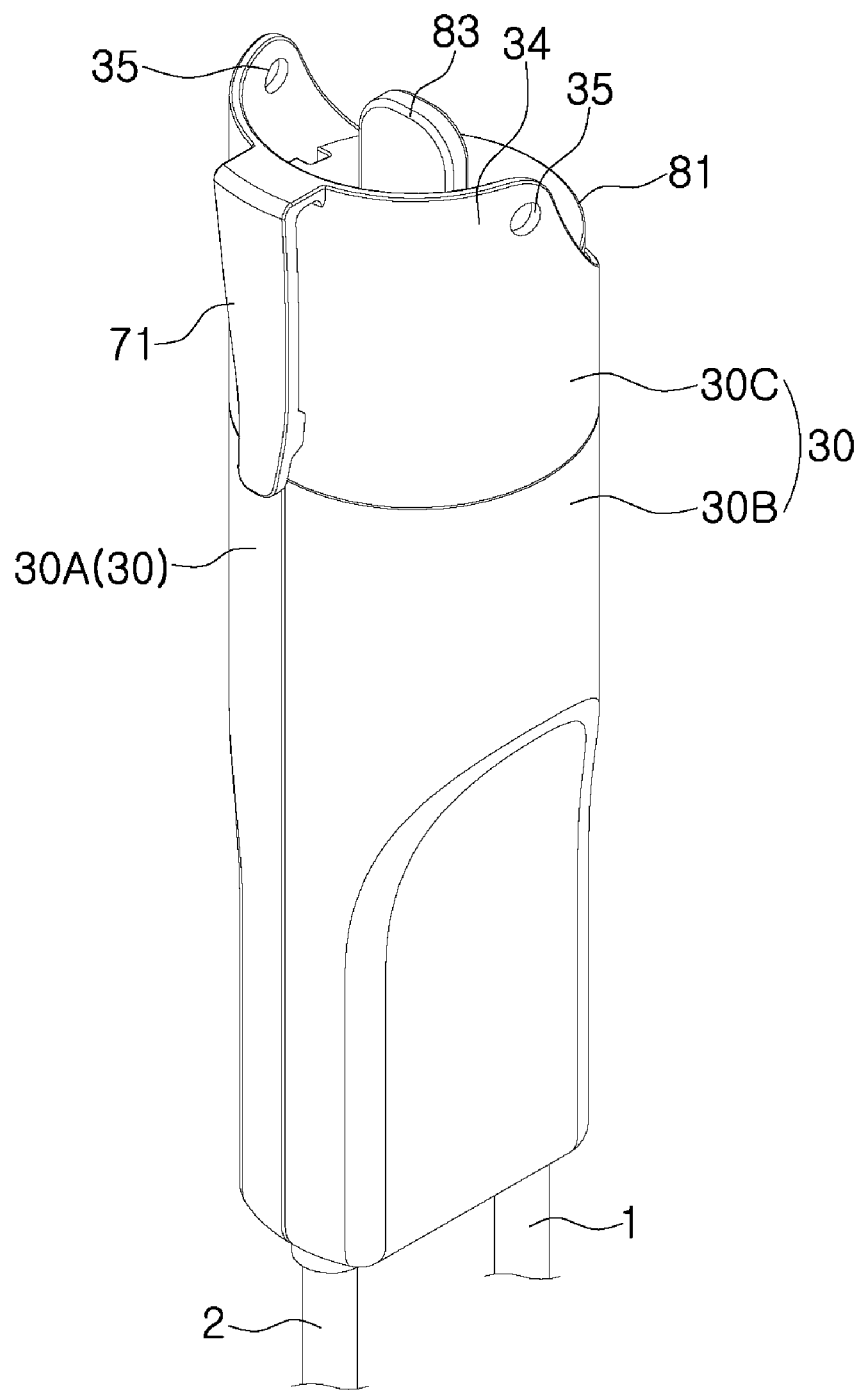
Figure 3:
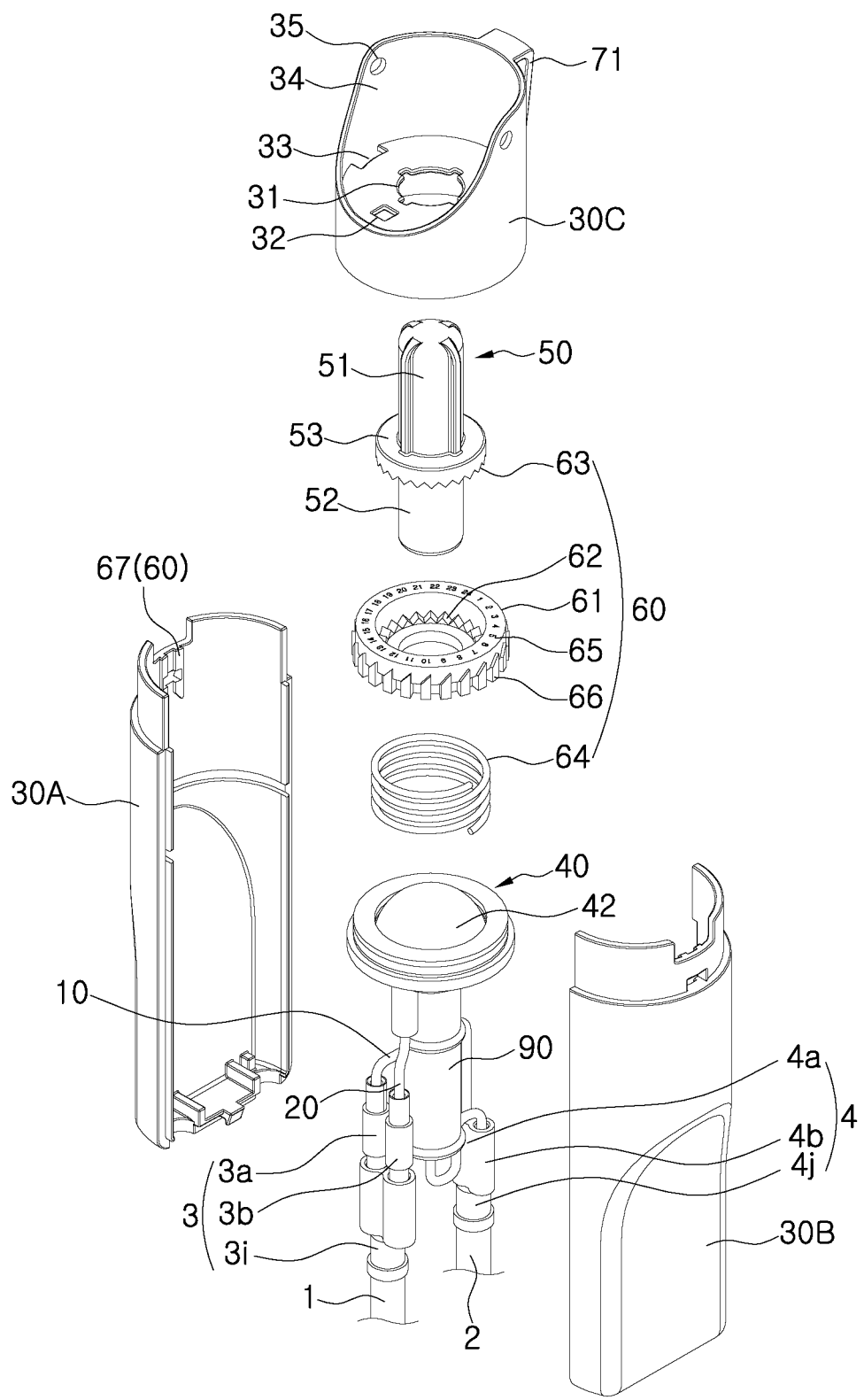
FIG. 3 is an exploded perspective view illustrating the medical fluid injector according to the first embodiment of the present invention.

In FIGS. 1 to 3, reference numerals 1 and 2 refer to a medical fluid inlet hose 1 and a medical fluid outlet hose 2, respectively. A medical fluid from a medical fluid supply source is provided to the patient via the medical fluid inlet hose 1 and the medical fluid outlet hose 2 sequentially. Referring to FIG. 3, the medical fluid inlet hose 1 is connected to a medical fluid branching mechanism 3, the medical fluid outlet hose 2 is connected to a medical fluid confluence mechanism 4. The medical fluid branching mechanism 3 and the medical fluid confluence mechanism 4 are connected to each other by first and second two transfer lines 10 and 20.

The medical fluid branching mechanism 3 includes a single inlet tube 3i having an inlet connected to the medical fluid inlet hose 1, and two flow control tubes 3a and 3b branched from the inlet tube 3i and connected to one ends of the two transfer lines 10 and 20, respectively. For reference, the two flow control tubes 3a and 3b may be capillary tubes. The medical fluid confluence mechanism 4 includes a single confluence tube 4j having an outlet to which the medical fluid outlet hose 2 is connected, and two branch tubes 4a and 4b branched from the confluence tube 4j and connected to the other ends of the two transfer lines 10 and 20, respectively. An injection unit (e.g., a needle or a catheter) for injecting a patient with a medical fluid may be connected to a front end of the medical fluid outlet hose 2. As the first transfer line 10 and the second transfer line 20, elastically deformable silicone tubes, PVC tubes, or the like may be used.

The medical fluid injector according to the first embodiment of the present invention includes a housing 30, a bolus bag 40, a bolus button 50, and a bolus counter 60, in addition to the medical fluid inlet hose 1, the medical fluid outlet hose 2, the medical fluid branching mechanism 3, the medical fluid confluence mechanism 4, the first transfer line 10, and the second transfer line 20 as described above.

Referring to FIGS. 1 and 3, the housing 30 includes housing bodies 30A and 30B each of which has an open upper end, and a housing cap 30C covering the respective open ends of the housing bodies 30A and 30B. The housing 30 includes an interior space defined by the housing bodies 30A and 30B and the housing cap 30C. The housing bodies 30A and 30B are comprised of a left body 30A and a right body 30B that are coupled to each other as a pair. The housing cap 30C is coupled the housing bodies 30A and 30B in a form covering the top of housing bodies so as to prevent the housing bodies 30A and 30B from being separated into the left body 30A and the right body 30B.

For reference, the medical fluid branching mechanism 3 may be disposed in a lower region in the interior space of the housing 30 so that the inlet of the inlet tube 3i is exposed externally through the bottom of the housing 30, i.e., lower ends of the housing bodies 30A and 30B. The medical fluid confluence mechanism 4 may be disposed in the lower region in the internal space of the housing 30 so that the outlet of the confluence tube 4j is exposed to externally through the bottom of the housing 30.

Figure 4:
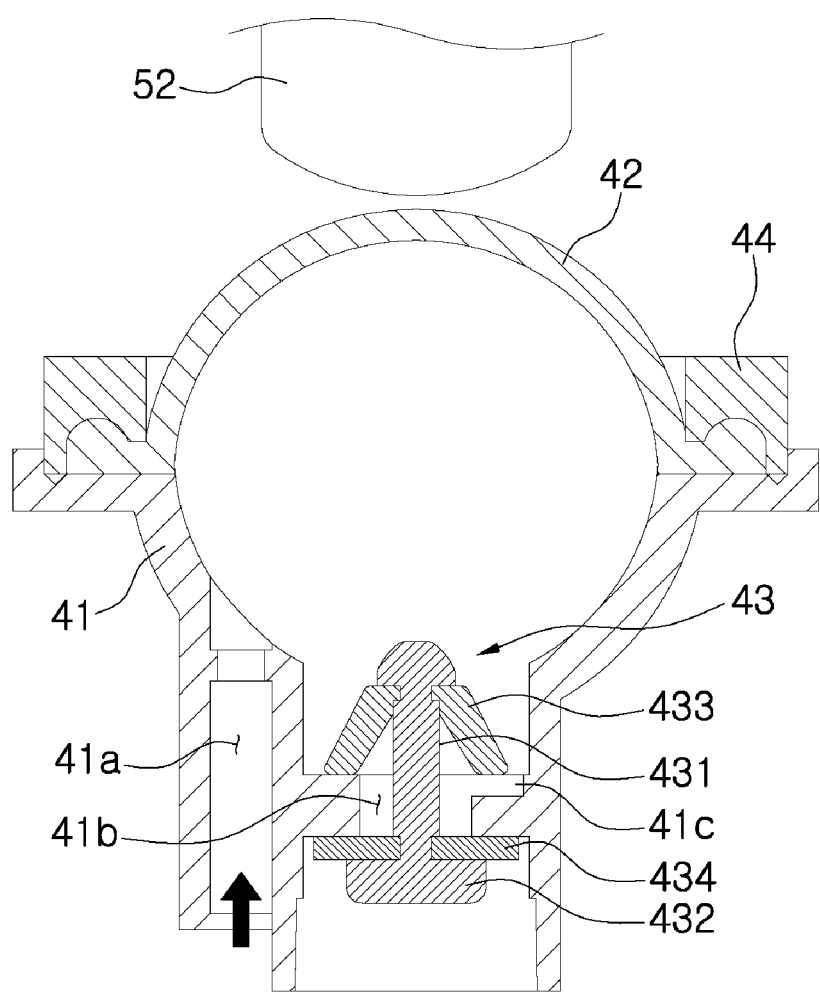
FIGS. 4 and 5 are sectional views illustrating the configuration and operation of a bolus bag illustrated in FIG. 3.
Figure 5:
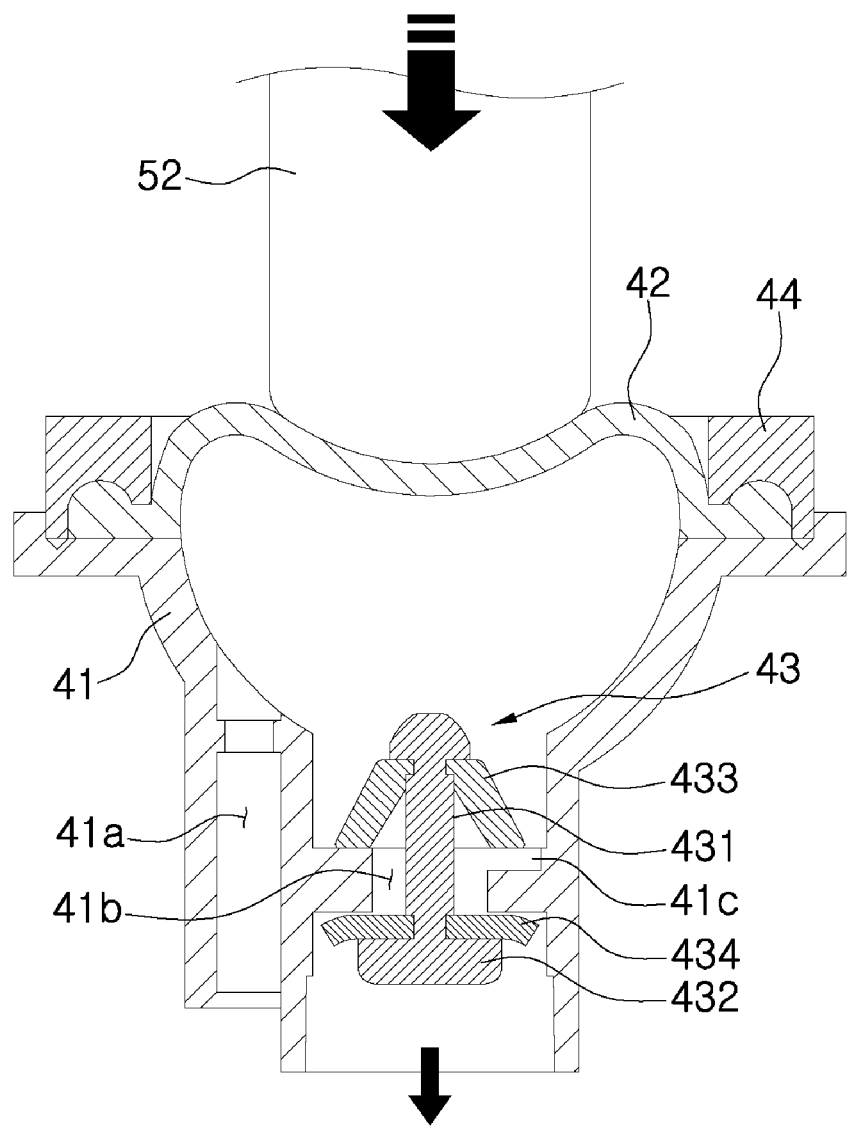

Referring to FIGS. 4, 5 and the like, the bolus bag 40 includes a container 41 having an upper open structure in which the medical fluid is stored, and an expansion sheet 42 for shielding an open upper portion of the container 41. The container 41 includes a medical fluid inlet 41a and a medical fluid outlet 41b, to which the second transfer line 20 is connected. In detail, the container 41 is configured to have a connection structure in which the medical fluid from an upstream side of the second transfer line 20 is introduced into the medical fluid inlet 41a and is stored in the container 41, and the medical fluid stored in the container 41 is discharged to a downstream side of the second transfer line 20 through the medical fluid outlet 41b.

The bolus bag 40 is fixed in position in a state of being accommodated in the interior space of the housing 30. The bolus bag 40 may be disposed in an intermediate region in the interior space of the housing 30.

As the expansion sheet 42, a sheet made of a silicone material may be used. The expansion sheet 42 is configured to be convexly expanded upwardly by the medical fluid introduced into the container 41 through the medical fluid inlet 41a, and to be restored to an original shape thereof when the medical fluid is discharged through the medical fluid outlet 41b. Of course, depending on the medical fluid storage capacity of the bolus bag 40, the expansion sheet 42 may remain flat without being convexly expanded upwardly even upon introduction of the medical fluid, be concavely deformed downwardly when pressurized in response to application of external force, and be restored to a flat shape by its own elasticity or by the medical fluid introduced into the container 41. The medical fluid outlet 41b is opened and closed by a check valve 43, and discharge of the medical fluid stored in the container 41 is restricted by the check valve 43. The check valve 43 is configured to be opened when the expanded expansion sheet 42 is pressurized in response to application of external force and the pressure in the container 41 increases thereby.

In FIGS. 4 and 5, reference numeral 44 denotes a closing cap constituting the bolus bag 40. The closing cap 44 is formed in a ring shape. The closing cap 44 is coupled to an upper end of the container 41. The closing cap 44 is ultrasonically fused to the container 41 with the expansion sheet 42 interposed between the closing cap 44 and the container 41, thereby preventing separation of the expansion sheet 42, and maintaining airtightness between the container 41 and the expansion sheet 42. Depending on the implementation conditions and the like, the closing cap 44 may be bolted to the container 41, rather than being ultrasonically fused to the container 41. Of course, the present invention is not limited to this, and therefore the closing cap 44 may be coupled to the container 41 in a variety of other ways to prevent separation of the expansion sheet 42 and to maintain airtightness between the container 41 and the expansion sheet 42.

The medical fluid from the medical fluid supply source is transferred along the medical fluid inlet hose 1, and then branched in the medical fluid branching mechanism 3 into two flows that are introduced into the first transfer line 10 and the second transfer line 20, respectively. The medical fluid from the first transfer line 10 is continuously injected into the patient sequentially through the medical fluid confluence mechanism 4 and the medical fluid outlet hose 2. The medical fluid introduced into the second transfer line 20 is stored in the bolus bag 40. The medical fluid in the bolus bag 40 is discharged from the bolus bag 40 to the downstream side of the second transfer line 20 when the expanded expansion sheet 42 is pressurized in response to application of external force, is combined with the medical fluid from the first transfer line 10 in the medical fluid confluence mechanism 4, and then is injected into the patient along the medical fluid outlet hose 2.

The check valve 43 includes lifting members (movable member) comprised of a lifting rod 431 and a base 432 provided at a lower end of the lifting rod 431. The lifting rod 431 and the base 432 may be integrally formed as a single body. The base 432 is formed to have a wider cross-sectional area than an outlet end of the medical fluid outlet 41b. The base 432 is disposed in a direction of the outlet end of the medical fluid outlet 41b, and the lifting rod 431 passes through the medical fluid outlet 41b so as to be movable along the medical fluid outlet 41b, with an upper end thereof disposed in a direction of an inlet end of the medical fluid outlet 41b.

The check valve 43 further includes a rubber cone 433 as an elastic member, and an elastic opening/closing member 434 opening and closing the outlet end of the medical fluid outlet 41b.

The rubber cone 433 imparts elastic force to the lifting members 431 and 432 to allow the lifting members 431 and 432 to move upwardly. The rubber cone 433 has a structure which is hollow with open upper and lower ends. An upper portion of the rubber cone 433 is coupled to the lifting rod 431 in a state fitted over the outer circumference of the lifting rod 431, with the lower end supported on a peripheral portion of the inlet end of the medical fluid outlet 41b. The lifting rod 431 may include a hook for preventing the rubber cone 433 from being separated.

The opening/closing member 434 is interposed between the outlet end of the medical fluid outlet 41b and the base 432, and is formed to have a larger cross-sectional area than the base 432. The opening/closing member is configured to be in close contact with a peripheral portion of the outlet end of the medical fluid outlet 41b by the action of the rubber cone 433 to maintain the medical fluid outlet 41b in a closed state.

In FIGS. 4 and 5, reference numeral 41c is a communication path formed as a groove that allows communication between the peripheral portion of the inlet end of the medical fluid outlet 41b and the inside of the medical fluid outlet 41b. The communication path 41c serves to prevent that delay or blockage of injection of the medical fluid into the medical fluid outlet 41b occurs due to the lower end of the rubber cone 433 that is in close contact with the peripheral portion of the inlet end of the medical fluid outlet 41b.

On the other hand, depending on the implementation conditions and the like, instead of the rubber cone 433, a spring may be used to impart elastic force to the lifting members 431 and 432 and to maintain the medical fluid outlet 41b in a closed state by the opening/closing member 434.

Referring to FIGS. 1 and 3, a button opening 31 is formed in the housing cap 30C constituting a ceiling of the housing 30 by passing through a central portion of an upper end of the housing cap from top to bottom, and the bolus button 50 is disposed in the button opening 31.

The bolus button 50 includes an upper button 51 inserted into the button opening 31 so as to be movable linearly in a vertical direction, a lower push rod 52 extending downwardly from the button 51 to have a straight structure, and a stop flange 53 provided between the button 51 and the push rod 52. The push rod 52 may be disposed in an upper region in the interior space of the housing 30.

The push rod 52 is configured, when the button 51 is pressed, to be moved downwardly together with the button 51 and pressurize the expanded expansion sheet 42 to cause the medical fluid in the bolus bag 40 to be discharged (see FIG. 5), and when the push rod 52 continues to be moved downwardly, the lifting members 431 and 432 are pressurized thereby. Upon pressurizing of the expanded expansion sheet 42, the opening/closing member 434 may be deformed by an internal pressure of the lifted bolus bag 40, causing the closed state of the medical fluid outlet 41b to be released. At this time, the lifting members 431 and 432 may be thereby moved downwardly to some extent. Upon pressurizing of the check valve 43, the lifting members 431 and 432 may be moved downwardly so that the opening/closing member 434 is spaced from the outlet end of the medical fluid outlet 41b and the peripheral portion thereof.

The stop flange 53 is configured to be in contact with a lower surface of the upper end of the housing cap 30C to restrict upward movement of the button 51.

The bolus counter 60 is configured to operate by a force that the button 51 is moved downwardly as the bolus button 50 is operated and to count the number of bolus injections according to the operation of the bolus button 50. The bolus counter 60 includes a count disc 61, first teeth 62, second teeth 63, an elastic member 64, a spacer 65, guide teeth 66, and at least one pair of guides 67.

Figure 6:
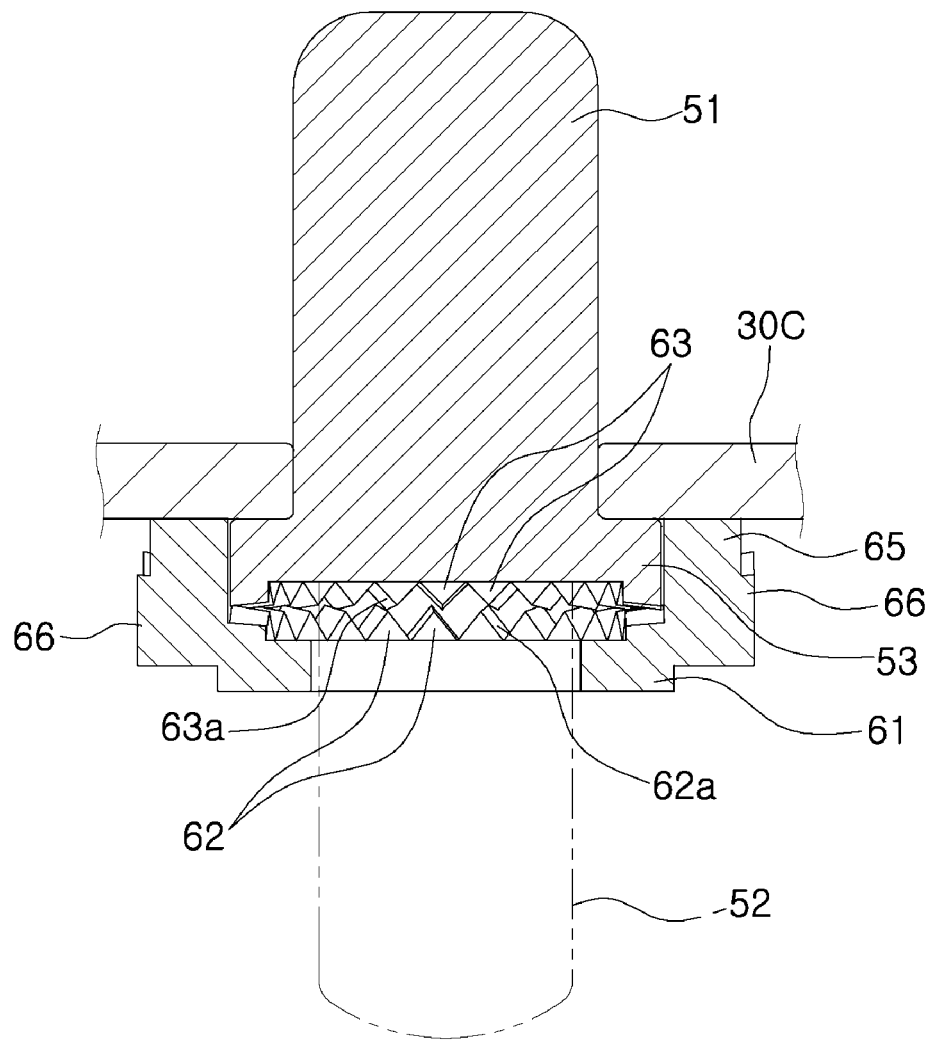
FIG. 6 is a sectional view illustrating a part of a bolus counter illustrated in FIG. 3.
Figure 7:
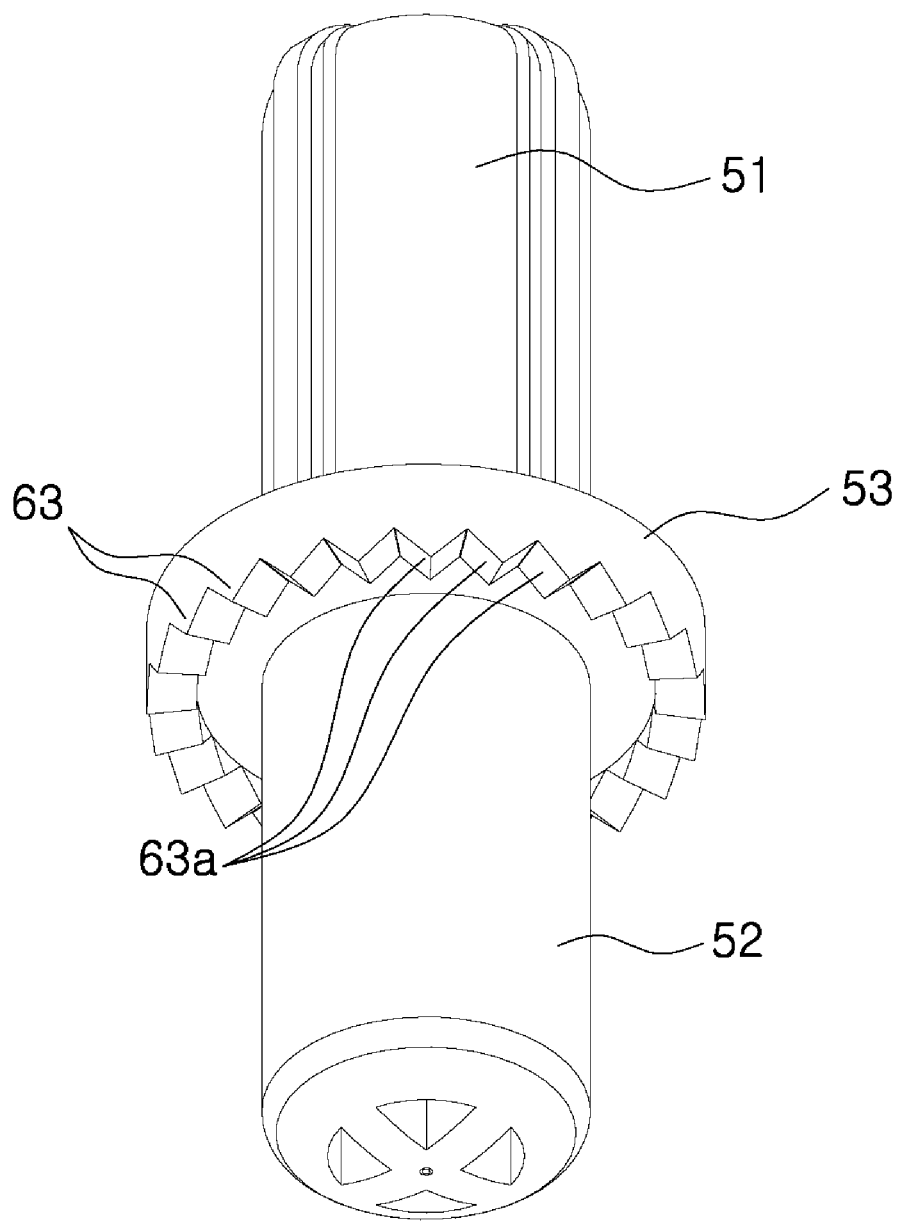
FIG. 7 is a perspective view illustrating a bolus button and second teeth illustrated in FIGS. 3 and 6.

Referring to FIG. 6, the count disc 61 is rotatably fitted over the outer circumference of the push rod 52 having a circular cross-section so as to be rotatable about the push rod 52. To this end, a through hole is formed in a central portion of the count disc 61 from top to bottom.

Figure 8:
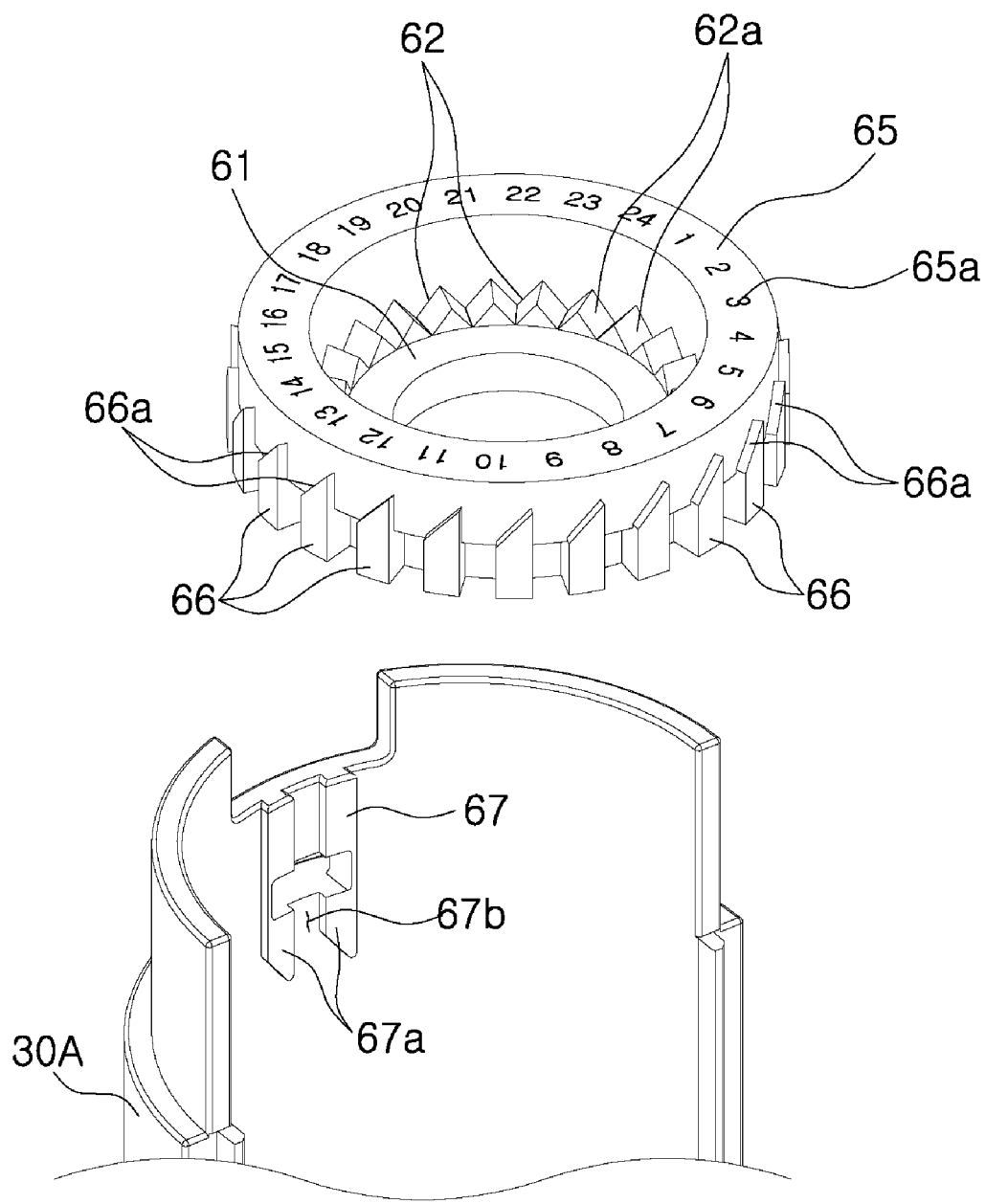
FIGS. 8 and 9 are perspective views illustrating a count disc, first teeth, a spacer, guide teeth, and a guide illustrated in FIGS. 3 and 6.

Referring to FIGS. 6 and 8, the first teeth 62 protrude to the same height from an upper surface of the count disc 61. The first teeth 62 are arranged on the upper surface of the count disc 61 in a circumferential direction at an interval of a predetermined angle (e.g., 24 first teeth may be arranged at an interval of 15 degree angles). Each of the first teeth 62 has a first inclined surface 62a inclined in the circumferential direction. The second teeth 63 protrude to the same height from a lower surface of the stop flange 53. The second teeth 63 are arranged on the lower surface of the stop flange 53 in a circumferential direction at the same interval of the predetermined angle as the first teeth 62. Each of the second teeth 63 has a second inclined surface 63a having a shape conforming to the first inclined surface 62a and is configured such that when the second teeth 63 are moved downwardly together with the stop flange 53, the respective second inclined surfaces 63a are brought into contact with the respective first inclined surfaces 62a to cause the count disc 61 to be rotated.

The elastic member 64 is a coil spring, and serves to impart a predetermined elastic force to the count disc 61 to allow the count disc 61 moved downwardly together with the bolus button 50 to be moved upwardly. In one example, the elastic member 64 may be configured such that an upper end thereof is supported on a lower side of the count disc 61 while a lower end thereof is supported on an upper side of the closing cap 44.

Referring to FIGS. 6 and 8, the spacer 65 protrudes to above the height of the first teeth 62 from a peripheral portion of the count disc 61 and is configured such that when the count disc 61 is moved upwardly by the elastic member 64, the spacer 65 is brought into contact with the lower surface of the upper end of the housing cap 30c to cause the first inclined surfaces 62a and the second inclined surfaces 63a corresponding to each other to be spaced apart from each other.

Figure 9:
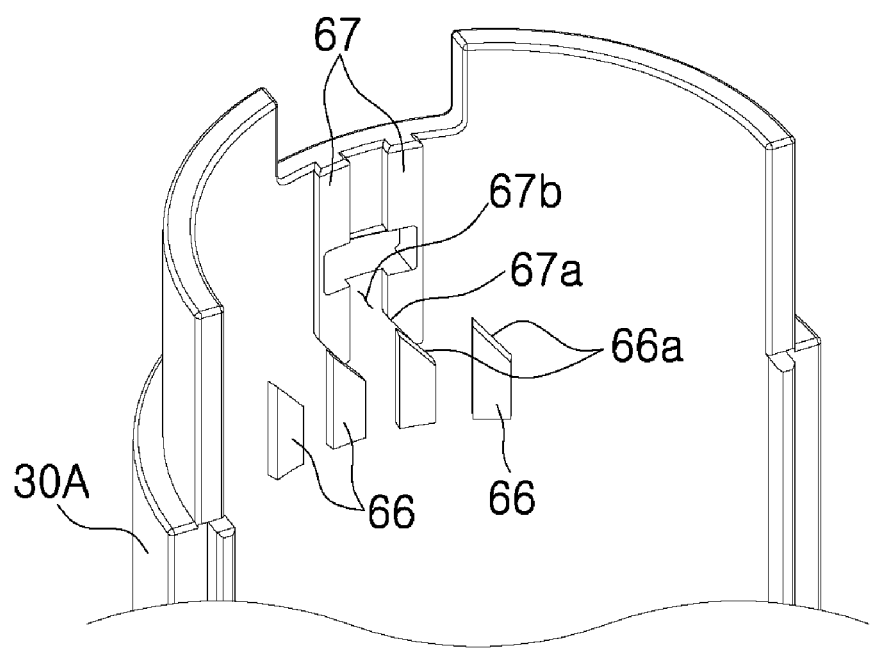

Referring to FIGS. 6, 8, and 9, the guide teeth 66 are arranged on an outer surface of the count disc 61 in a circumferential direction at the same interval of the predetermined angle as the first teeth 62. Each of the guide teeth 66 has a first guide surface 66a formed at an upper portion thereof to be inclined in the same circumferential direction as the first inclined surface 62a. The pair of guides 67 is configured such that a guide groove 67b into which at least one of the guide teeth 66 is fitted when the count disc 61 is moved upwardly by the elastic member 64 is provided on the inner circumference of the housing 30, and a second guide surface 67a corresponding to the first guide surface 66a is formed at a lower portion of each of the guides.

In the bolus counter 60 as described above, when the count disc 61 is moved downwardly by a pressing operation of the button 51, the count disc is rotated by a partial angle (e.g., 7.5 degree angles) of the predetermined angle by the first inclined surfaces 62a and the second inclined surfaces 63a corresponding to each other. That is, referring to FIG. 6, upon the movement of the count disc, the first inclined surfaces 62a are brought into contact with the second inclined surfaces 63a while pressurizing the second inclined surfaces 63a, thereby causing the count disc 61 to be rotated while being moved together with the button 51.

On the contrary, when the count disc 61 is moved upwardly by the elastic member 64 as the pressing operation of the button 51 is released, the count disc is rotated by a remaining angle (e.g., 7.5 degree angles) of the predetermined angle by the first guide surfaces 66a and the second guide surfaces 67a to a position where the second inclined surfaces 63a correspond to the other first inclined surfaces 62a neighboring thereto. At this time, the rotation of the count disc 61, referring to FIG. 9, is made by an action that the respective first guide surfaces 66a continue to move upwardly while in contact with the respective second guide surfaces 67a. In this process, the button 51 is also moved upwardly.

Of course, when the button 51 is pressed again thereafter, the count disc 61 is rotated again by the predetermined angle to a position where the second inclined surfaces 63a correspond to the next first inclined surfaces 62a neighboring thereto, whereby the count disc 61 is set to be rotated again by the predetermined angle when the button 51 is pressed again. Therefore, the count disc 61 can be rotated by the predetermined angle only by the pressing operation of the button 51.

For reference, FIG. 9 illustrates only a part of guide teeth 66 by excluding the count disc 61, the spacer 65, and the like in order to describe a coupling relationship between the first guide surfaces 66a and the second guide surfaces 67a.

As illustrated in FIG. 8, the spacer 65 is formed in a ring shape, with an upper surface provided with an indicator 65a for indicating the number of bolus injections. The indicator 65a may be a series of numbers that are marked on an upper surface of the spacer 65 in a circumferential direction at an interval of a predetermined angle. As illustrated in FIG. 1, a number indicating opening 32 exposing the indicator 65a is provided at the upper end of the housing cap 30C. The number indicating opening 32 may be formed to have a size that allows only a number indicating a corresponding number of bolus injections to be exposed.

Referring to FIG. 1, a button cover 34 protecting a button 51 protruding through the button opening 31 is formed at the upper end of the housing cap 30C so as to entirely surround remaining regions except for any one of peripheral regions around the button 51. By the provision of the button cover 34, it is possible to prevent that the button 51 is pressed unintentionally for bolus injection.

As illustrated in FIG. 2, the button cover 34 may be provided with a clip 71 for carrying purposes. Alternatively, a string connection hole 35 may be provided as a hole for connection of a portable string 72.

Referring to FIG. 3, the medical fluid injector according to the first embodiment of the present invention further includes a medical fluid continuous discharge means 90 configured to temporarily store the medical fluid from the bolus bag 40 and continuously discharge the temporarily stored medical fluid to the medical fluid outlet hose 2 so that the medical fluid is additionally provided to the patient for a predetermined period of time without reoperation of the bolus button 50. The medical fluid continuous discharge means 90 may be connected to the medical fluid outlet 41b of the container 41 constituting the bolus bag 40 and to an inlet end of the downstream side of the second transfer line 20 so as to allow the medical fluid to flow therethrough. Furthermore, the medical fluid continuous discharge means 90 may be disposed in the lower region in the interior space of the housing 30.

The medical fluid continuous discharge means 90 includes a balloon and a backflow prevention mechanism, and is configured such that when the button 51 of the bolus button 50 is pressed, the medical fluid to be additionally administered to the patient is introduced into the balloon and the balloon is expanded thereby to cause the medical fluid to be stored therein, and then the balloon is contracted by its own restoring force to cause the stored medical fluid to be discharged, and upon discharging of the medical fluid, backflow is prevented by the backflow prevention mechanism. The medical fluid continuous discharge means 90 is configured and operates substantially the same or similar to a medical fluid continuous discharge means disclosed in Korean Patent No. 10-1126213, and therefore a detailed description thereof will be omitted herein.

In FIG. 1, reference numeral 80 denotes a button holder for maintaining a pressurized state of the bolus bag 40 pressurized by the button 51 moved downwardly.

The button holder 80 includes a plate-shaped body 81 for pressing the button 51, and legs 82 arranged at a lower portion of the body in a circumferential direction and each of which has a lower end bent in the circumferential direction. A handle 83 may be provided at an upper portion of the body 81. The handle 83 may be formed in a shape protruding upwardly. The handle 83 is operable by a user to facilitate handling of the button holder 80.

Slots 33 into which the respective legs 82 of the button holder 80 are inserted from top to bottom are provided at the upper end of the housing cap 30C in a circumferential direction at a regular interval. The legs 82 are configured to be prevented from separation (upward movement) when inserted into the slots 33 and rotated, and have a length that allows the button 51 to be pressed by the body 81 when the respective lower ends of the legs are caught in the slots 33. Upon pressing of the button, the push rod 52 pressurizes the check valve 43 to cause the lifting members 431 and 432 to be moved downwardly so that the opening/closing member 434 is spaced from the outlet end of the medical fluid outlet 41b and the peripheral portion thereof.

By the provision of the button holder 80 configured as above, the medical fluid injector according to the present invention is advantageous in that since the bolus bag 40 is maintained in a pressurized state, during a priming operation of, prior to administrating the medical fluid to the patient, flowing the medical fluid through a medical fluid flow path (the medical fluid inlet hose 1, the medical fluid outlet hose 2, the medical fluid branching mechanism 3, the medical fluid confluence mechanism 4, and the transfer lines 10 and 20) to discharge air from the medical fluid flow path, it is possible to drastically reduce the time that the medical fluid is stored in the bolus bag 40, thereby performing the priming operation quickly.

The medical fluid injector according to the first embodiment of the present invention is used with the button holder 80 removed after the priming operation is completed.

Figure 10:
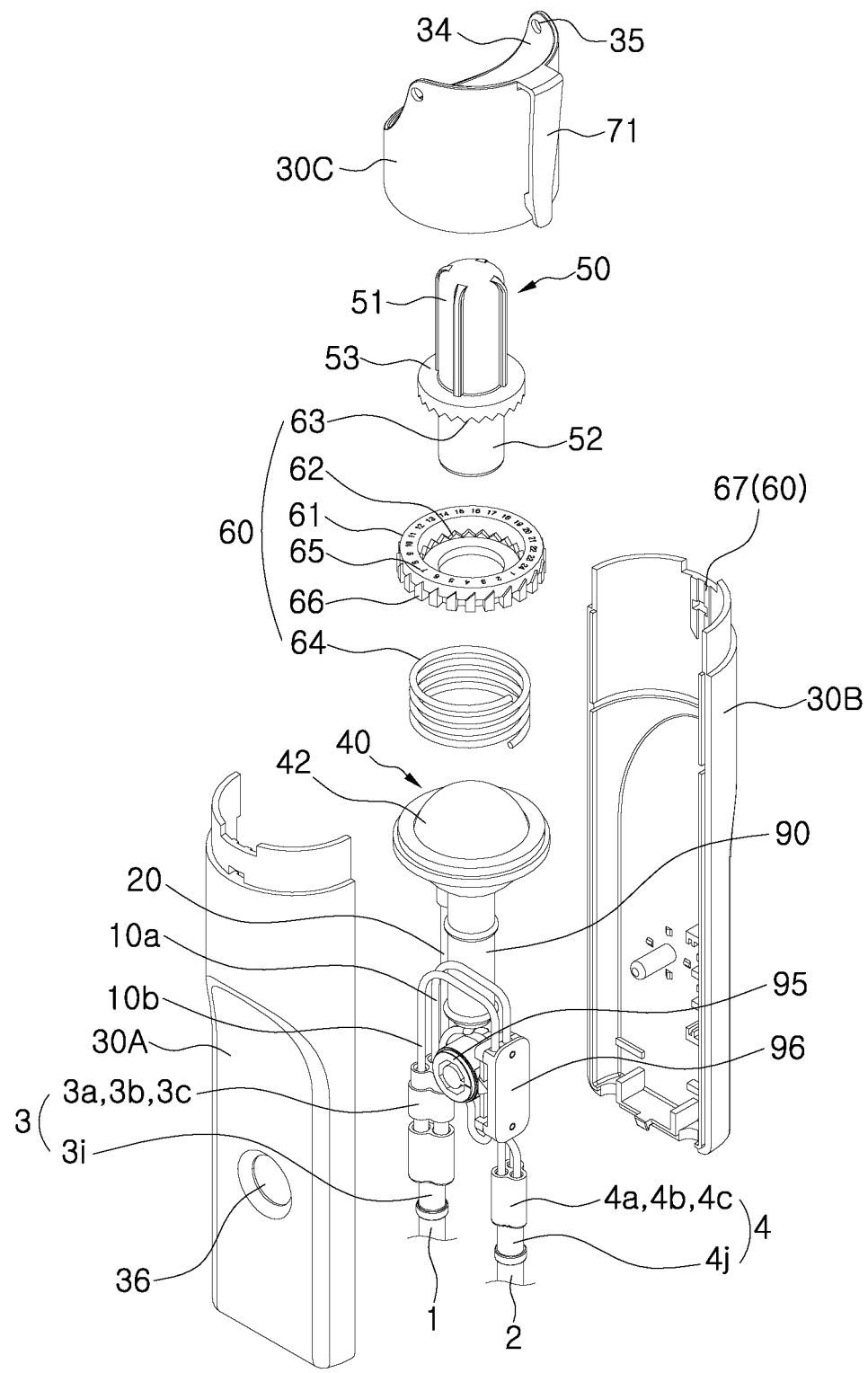
FIG. 10 is an exploded perspective view illustrating a medical fluid injector according to a second embodiment of the present invention.

FIG. 10 illustrates a medical fluid injector according to a second embodiment of the present invention. As illustrated in FIG. 10, the medical fluid injector according to the second embodiment of the present invention remains the same the first embodiment of the present invention in terms of other configurations and operations, but differs only in that a flow rate control device 95 and 96 is further provided to control the flow rate of a medical fluid continuously injected into a patient through first transfer lines 10a and 10b.

The first transfer lines 10a and 10b are provided in plural numbers, and accordingly, a medical fluid branching mechanism 3 and a medical fluid confluence mechanism 4 include at least three flow control tubes 3a, 3b, and 3c and at least three branch tubes 4a, 4b, and 4c, respectively. Among the flow control tubes 3a, 3b, and 3c, flow control tubes connected to the respective first transfer lines 10a and 10b are configured to allow the medical fluid to flow therethrough at different flow rates.

The flow control devices 95 and 96 include a rotatable knob 95, and a tube opening/closing means 96 for selectively opening and closing the first transfer lines 10a and 10b according to an angle at which the knob 95 is rotated to open both the first transfer lines 10a and 10b or at least one of the first transfer lines 10a and 10b.

Reference numeral 36 denotes a knob opening. The knob 95 rotatably disposed in an interior space of a housing 30 is exposed externally through the knob opening 36 of housing bodies 30A and 30B.

The flow control devices 95 and 96 and related configurations thereof are configured and operate substantially the same or similar to flow control devices disclosed in Korean Patent Nos. 10-1638969 and 10-1739368, and a more detailed description thereof will be omitted herein.

What is claimed is:

1. A medical fluid injector, comprising:
   a housing having an upper end provided with a button opening;
   a bolus bag connected to a medical fluid transfer line to store a medical fluid from an upstream side and discharge the stored medical fluid to a downstream side, and disposed inside the housing;

a bolus button including a button movably inserted into the button opening so at to be movable upwardly and downwardly, and a push rod extending downwardly from the button and configured to push the bolus bag to cause the medical liquid in the bolus bag to be discharged when the button is moved downwardly; and a bolus counter configured to operate with a force that the button is moved downwardly and count the number of bolus injections according to operation of the bolus button, wherein the bolus button comprises a stop flange provided between the button and the push rod, the stop flange having an upper surface configured to be in contact with the upper end of the housing to restrict upward movement of the button, wherein the bolus counter comprises:
   a count disc rotatably fitted over an outer circumference of the push rod;
   first teeth arranged on an upper surface of the count disc at an interval of a predetermined angle in a circumferential direction, and each of which includes a first inclined surface inclined in the circumferential direction;
   at least one second tooth provided on a lower surface of the stop flange to have a second inclined surface corresponding to the first inclined surface, and configured such that when the second tooth is moved downwardly, the second inclined surface is brought into contact with the first inclined surface to cause the count disc to be rotated;
   an elastic member placed below the counter disc for imparting elastic force to the count disc to allow the count disc to be moved upwardly;
   a spacer unitarily formed on the counter disc and protruded to above a height of the first teeth from a peripheral portion of the count disc and configured such that when the count disc is moved upwardly by the elastic member, the spacer is brought into contact with a lower surface of the upper end of the housing to cause the first inclined surface and the second inclined surface corresponding to each other to be spaced apart from each other;
   guide teeth arranged on an outer surface of the count disc in a circumferential direction at the interval of the predetermined angle, and each of which has a first guide surface formed at an upper portion thereof to be inclined in the same circumferential direction as the first inclined surface; and
   a guide provided on an inner circumference of the housing and configured such that a guide groove into which at least one of the guide teeth is fitted when the count disc is moved upwardly by the elastic member, wherein a second guide surface corresponding to the first guide surface is formed at a lower end portion of the guide,
   wherein when the count disc is moved downwardly by the bolus button, the count disc is rotated by a partial angle of the predetermined angle by the first inclined surface and the second inclined surface corresponding to each other, and when the count disc is moved upwardly by the elastic member, the count disc is rotated by a remaining angle of the predetermined angle by the first guide surface and the second guide surface to a position where the second inclined surface corresponds to the other first inclined surface neighboring thereto.

2. The medical fluid injector of claim 1, wherein the spacer is formed in a ring shape, with an upper surface provided with an indicator indicating the number of bolus injections, and
   a number indicating opening exposing the indicator is provided at the upper end of the housing.

3. The medical fluid injector of claim 1, wherein the bolus bag comprises:
   a container having a medical fluid inlet and a medical fluid outlet, with an open upper portion;
   an expansion sheet shielding the open upper portion of the container; and
   a check valve opening and closing the medical fluid outlet,
   wherein the expansion sheet is configured to be expanded by the medical fluid introduced into the container through the medical fluid inlet, and
   the check valve comprises:
   a movable member passing through the medical fluid outlet so as to be movable along the medical fluid outlet;
   an opening/closing member coupled to the movable member to open and close an outlet end of the medical fluid outlet according to a moving direction of the movable member; and
   an elastic member imparting elastic force to the movable member in a direction in which the opening/closing member is closed,
   wherein when the expansion sheet is pressurized by the push rod and a pressure in the container is increased thereby, the movable member is moved while overcoming the elastic force of the elastic member of the check valve in a direction in which the opening/closing member is opened, thereby causing the medical fluid outlet to be opened.

4. The medical fluid injector of claim 1, wherein a button cover protecting the button protruding through the button opening is formed at the upper end of the housing so as to entirely surround remaining regions except for any one of peripheral regions around the button.

5. The medical fluid injector of claim 1, further comprising:
   a button holder maintaining a pressurized state of the bolus bag pressurized by the button moved downwardly,
   wherein the button holder comprises:
   a body pressing the button; and legs arranged at a lower portion of the body in the circumferential direction, and each of which has a lower end bent in a circumferential direction,
   slots into which the respective legs are inserted are provided at the upper end of the housing in a circumferential direction, and
   the legs are configured to be prevented from separation when inserted into the slots and rotated, and have a length that allows the button to be pressed by the body when the respective lower ends of the legs are caught in the slots.

\* \* \* \* \*